(12) United States Patent
Ernst et al.

(10) Patent No.: US 8,461,391 B2
(45) Date of Patent: Jun. 11, 2013

(54) METHOD FOR PRODUCING N,N-SUBSTITUTED-1,3-PROPANDIAMINES

(75) Inventors: Martin Ernst, Heidelberg (DE); Johann-Peter Melder, Böhl-Iggelheim (DE); Christof Wilhelm Wigbers, Mannheim (DE)

(73) Assignee: BASF SE (DE)

( * ) Notice: Subject to any disclaimer, the term of this patent is extended or adjusted under 35 U.S.C. 154(b) by 245 days.

(21) Appl. No.: 12/991,767

(22) PCT Filed: May 11, 2009

(86) PCT No.: PCT/EP2009/055655
§ 371 (c)(1),
(2), (4) Date: Nov. 9, 2010

(87) PCT Pub. No.: WO2009/138377
PCT Pub. Date: Nov. 19, 2009

(65) Prior Publication Data
US 2011/0060166 A1  Mar. 10, 2011

(30) Foreign Application Priority Data

May 13, 2008 (EP) ................... 08156092
Nov. 5, 2008 (EP) ................... 08168393

(51) Int. Cl.
*C07C 209/60* (2006.01)

(52) U.S. Cl.
USPC ............... 564/471; 564/446; 564/485

(58) Field of Classification Search
None
See application file for complete search history.

(56) References Cited

U.S. PATENT DOCUMENTS

| | | | |
|---|---|---|---|
| 2,558,520 A | 6/1951 | Hoyt et al. | |
| 2,565,488 A | 8/1951 | Finch et al. | |
| 3,383,392 A | 5/1968 | Mawer | |
| 5,079,266 A | 1/1992 | Bockowski et al. | |
| 5,371,292 A | 12/1994 | Merger et al. | |
| 5,426,249 A | 6/1995 | Haas et al. | |
| 5,536,691 A | 7/1996 | Breitscheidel et al. | |
| 5,696,048 A | 12/1997 | Breitscheidel et al. | |
| 6,525,222 B2 | 2/2003 | Nouwen et al. | |
| 6,660,887 B1 | 12/2003 | Ward et al. | |
| 6,982,352 B2 * | 1/2006 | Lappe et al. | ........ 564/471 |
| 7,183,438 B2 | 2/2007 | Gerlach et al. | |
| 7,531,699 B2 | 5/2009 | Dubois | |
| 2009/0149314 A1 | 6/2009 | Ernst et al. | |

FOREIGN PATENT DOCUMENTS

| | | |
|---|---|---|
| CA | 2105100 | 3/1994 |
| CN | 1594109 A | 3/2005 |
| DE | 866647 C | 2/1953 |
| DE | 4232424 A1 | 3/1994 |
| EP | 0449089 A1 | 10/1991 |
| EP | 0590419 A1 | 4/1994 |
| EP | 598228 A1 | 5/1994 |
| EP | 0636409 A1 | 2/1995 |
| EP | 0742045 A1 | 11/1996 |
| EP | 0963975 A1 | 12/1999 |
| EP | 1106600 A2 | 6/2001 |
| EP | 1852182 A1 | 11/2007 |
| WO | WO-03/076386 A2 | 9/2003 |
| WO | WO-2004/060853 A1 | 7/2004 |
| WO | WO-2006/087083 A2 | 8/2006 |
| WO | WO-2007/090990 A2 | 8/2007 |
| WO | WO-2007/104663 A1 | 9/2007 |

* cited by examiner

*Primary Examiner* — Brian J Davis
(74) *Attorney, Agent, or Firm* — Novak Druce Connolly Bove + Quigg LLP

(57) ABSTRACT

The present invention relates to a process for preparing N,N-substituted 1,3-propanediamine by
a) reacting secondary amine with acrolein at a temperature of from (−50) to 100° C. and a pressure of from 0.01 to 300 bar, and
b) reacting the reaction mixture obtained in stage a) with hydrogen and ammonia in the presence of a hydrogenation catalyst at a temperature of from 40 to 400° C. and a pressure of from 1 to 400 bar,
wherein the molar ratio of secondary amine to acrolein in stage a) is 2:1 or more and the hydrogenation catalyst used in stage b) comprises cobalt. In a preferred embodiment, acrolein which has been obtained from glycerol based on renewable raw materials is used. The invention further relates to the use of N,N-dimethyl-1,3-propanediamine (DMAPA) based on renewable raw materials as a feedstock for lubricant soaps and other detergents, coagulants, polymers and comb polymers. In a further preferred embodiment, stage b) is performed in the presence of water.

15 Claims, No Drawings

METHOD FOR PRODUCING N,N-SUBSTITUTED-1,3-PROPANDIAMINES

CROSS-REFERENCE TO RELATED APPLICATIONS

This application is a national stage application (under 35 U.S.C. §371) of PCT/EP2009/055655, filed May 11, 2009, which claims benefit of European application 08168393.0, filed May 23, 2008, and European application 08156092.2, filed May 13, 2008.

BACKGROUND OF THE INVENTION

The invention relates to a process for preparing N,N-substituted 1,3-propanediamines.

N,N-Substituted 1,3-propanediamines are obtained typically by reacting secondary amines with acrylonitrile and subsequently hydrogenating the nitrile group to the amine. For example, the industrially significant N,N-dimethyl-1,3-propanediamine (DMAPA) is prepared on the basis of dimethylamine and acrylonitrile. The acrylonitrile starting material is typically obtained by the SOHIO process, a catalytically controlled synthesis of propene with ammonia and elemental oxygen. This forms acrylonitrile with elimination of water, with acetonitrile and hydrogen cyanide as by-products.

Access to chemical commodity products such as propene from renewable raw materials is generally uneconomic, since the complex molecular structures formed by nature with considerable energy expenditure can be reshaped to low molecular weight substances only with expenditure of energy. A low molecular weight chemical commodity product which, however, can be obtained commercially from renewable raw materials is acrolein, which is prepared by dehydrating glycerol. Glycerol in turn is obtained typically as a by-product in the conversion of fats and oils to fatty acids (fat hydrolysis) or fatty acid methyl esters (biodiesel).

The reaction of secondary aliphatic amines with acrolein was described for the first time by Mannich et al. (C. Mannich, K. Handke and K. Roth, Chem. Ber., 69, 2112 (1936)). Reaction of dimethylamine with acrolein in the presence of a dehydrating agent or in a water-immiscible solvent afforded, within a narrow pressure and temperature range, N,N,N',N'-tetramethyl-1,3-propenediamine, which was converted further in a further stage by catalytic reduction with hydrogen over platinum oxide and cyclohexane as a solvent to the corresponding N,N,N',N'-tetramethyl-1,3-propanediamine. According to the disclosure, the water which forms in the reaction has to be removed from the reaction mixture since the products which form are readily hydrolyzable. Some of the N,N,N',N'-tetramethyl-1,3-propanediamines obtained by the reaction described by Mannich et al. are used as catalysts in the preparation of polyurethanes.

A process for reacting primary aliphatic or cycloaliphatic amines with acrolein to give N,N'-substituted 1,3-propenediamines is likewise disclosed in U.S. Pat. No. 2,565,488 and in the equivalent DE-B-866647. The amounts of water which form in the reaction can, according to the disclosure, be left in the reaction mixture. When the reaction, however, is performed in the presence of dehydrating agents (desiccants), higher yields of N,N'-substituted 1,3-propenediamine are achieved. It is stated that N,N'-substituted 1,3-propenediamines can be saturated with hydrogen, so as to obtain, for example, N,N'-substituted 1,3-propanediamines. It is also stated that N,N'-substituted 1,3-propenediamines can be transaminated with amines which comprise other substituents in a further reaction step before the hydrogenation.

DE-A1-4232424 relates to a process for preparing N,N'-substituted or N,N,N',N'-substituted unsaturated amines by reacting 2-alkenals with primary or secondary amines at temperatures of from (−20) to 70° C. and pressures of from 0.10 to 100 bar, by performing the reaction without removing the water of reaction. In addition, the disclosure describes the transamination of the unsaturated amines thus obtained by the reaction thereof with other primary or secondary amines at temperatures of from 20 to 150° C. The unsaturated amines obtained in DE-A1-4232424 can, according to the disclosure, be hydrogenated with hydrogen at a pressure of from 1 to 350 bar and temperatures of from 0 to 150° C., using, for example, palladium supported on activated carbon as the hydrogenation catalyst.

Finch et al. (H. D. Finch, E. A. Peterson and S. A. Ballard, J. Am. Chem. Soc., 74, 2016 (1952)) describe the reaction of acrolein or methacrolein with primary or secondary amines. The N,N'-substituted 1,3-propenediamines or N,N,N',N'-substituted 1,3-propenediamines thus obtained are, according to the disclosure, hydrogenated in a subsequent stage to the corresponding saturated N,N'-substituted or N,N,N',N'-substituted 1,3-propanediamines, or heated together with other amines, such that an amine exchange takes place. It is stated that amine exchange and hydrogenation can also be carried out simultaneously in the presence of a Raney® nickel catalyst. For instance, N-isopropyl-1,3-propanediamine was obtained in two stages, the first stage involving initial reaction of acrolein with isopropylamine and the second stage hydrogenation of the resulting reaction mixture, after removal of excess amine and solvent, with ammonia in the presence of Raney® nickel. The yields of N-isopropyl-1,3-propanediamine, based on the acrolein used in the reaction, were less than 68%.

The problem of the present invention consisted in providing a process for preparing N,N-substituted 1,3-propanediamines from acrolein, the intention having been to achieve a higher selectivity based on the acrolein used as compared with the prior art. More particularly, it was an object of the invention to reduce the formation of by-products, such as 3-methylpiperidine and N,N,N',N'-substituted 1,3-propanediamines, which can form in the hydrogenation of the N,N,N',N'-substituted 1,3-propenediamines which form as an intermediate. It was a further aim to provide a process in which the N,N,N',N'-substituted 1,3-propenediamines obtained as an intermediate need not be isolated or purified before the further conversion to N,N-substituted 1,3-propanediamine. The intention was thus to achieve an easy to handle process which can be implemented in a technically simple manner. More particularly, it was an aim of the present invention to provide a new preparation route for DMAPA, in which feedstocks which can be obtained on the basis of renewable raw materials are used.

BRIEF SUMMARY OF THE INVENTION

According to the invention, the object is achieved by a process for preparing N,N-substituted 1,3-propanediamine by
a) reacting secondary amine with acrolein at a temperature of from (−50) to 100° C. and a pressure of from 0.01 to 300 bar, and
b) reacting the reaction mixture obtained in stage a) with hydrogen and ammonia in the presence of a hydrogenation catalyst at a temperature of from 40 to 400° C. and a pressure of from 1 to 400 bar, wherein the molar ratio of secondary amine to acrolein in stage a) is 2:1 or more and the hydrogenation catalyst used in stage b) comprises cobalt.

In the first stage a) of the process according to the invention, acrolein is reacted with secondary amine.

DETAILED DESCRIPTION OF THE INVENTION

The acrolein used in the reaction is typically obtained by oxidizing propene or by dehydrating glycerol.

Typically, acrolein is obtained by oxidizing propene. An overview of acrolein preparation by propene oxidation can be found, for example, in the Ullmann (Ullmann's Encyclopedia of Industrial Chemistry, Acrolein and Methacrolein, Chapter 3.1 "Acrolein by Propene Oxidation", Wiley-VCH-Verlag, Electronic Edition, 2007).

In a preferred embodiment, acrolein which has been obtained by dehydrating glycerol is used. The preparation of acrolein by dehydrating glycerol is disclosed, for example, in WO-A2-2006087083, EP-B1-598228, WO-A1-2007090990, U.S. Pat. No. 5,079,266, U.S. Pat. No. 2,558,520 or by Chai et al. (S. H. Chai, H. P. Wang, Y. Lang, B. Q. Xu, Journal of Catalysis, 250 (2), 342-349 (2007)).

Glycerol is obtained typically as a by-product in the conversion of fats and oils to fatty acids (fat hydrolysis) or fatty acid methyl esters (biodiesel). The preparation of glycerol from fats and oils is described, for example, in the Ullmann (Ullmann's Encyclopedia of Industrial Chemistry, Glycerol, Chapter 4.1 "Glycerol from Fat and Oils", Wiley-VCH-Verlag, Electronic Edition, 2007).

Glycerol can also be prepared proceeding from the petrochemical starting material of propene. An overview of the synthesis of glycerol from propene is likewise given in the Ullmann (Ullmann's Encyclopedia of Industrial Chemistry, "Glycerol", Chapter 4.1 "Synthesis from Propene", Wiley-VCH-Verlag, Electronic Edition, 2007). For the process according to the invention, the preparation route by which glycerol has been obtained is generally unimportant. Glycerol on a vegetable, animal or petrochemical basis is suitable as a starting material for the process according to the invention.

In a very particularly preferred embodiment, glycerol based on renewable raw materials is used as the starting material in the preparation of acrolein, for example glycerol obtained as a by-product from fat hydrolysis or biodiesel production. This particular embodiment has the advantage that industrially significant amines, such as DMAPA, can be obtained from renewable resources. The use of renewable resources in the preparation of such products can contribute to preservation of the petrochemical resources which are typically used.

Preference is given to using, in the process according to the invention, acrolein with an acrolein content of at least 95%, preferably at least 98% and more preferably at least 99%.

A further feedstock used in the process according to the invention is secondary amine.

The secondary amines used may be aliphatic, cycloaliphatic or cyclic secondary amines.

The cyclic secondary amine used may, for example, be pyrrolidine, imidazole, piperidine, morpholine or piperazine.

Preference is given to using secondary amines of the formula (I)

where the $R^1$ and $R^2$ radicals are each defined as follows:
$R^1$ and $R^2$ are identically or each independently a straight-chain or branched or a cyclic hydrocarbon radical having from 1 or 3 to 20 carbon atoms, where the hydrocarbon radical may be mono- or polyunsaturated.

For example, $R^1$ and/or $R^2$ may be defined as follows:
$C_1$-$C_6$-alkyl: e.g. methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl or 1-ethyl-3-methylpropyl;

$C_1$-$C_{12}$-alkyl: e.g. $C_1$-$C_6$-alkyl as specified above, and also heptyl, 2-methylhexyl, 3-methylhexyl, 2,2-dimethylpentyl, 2,3-dimethylpentyl, 2,4-dimethylpentyl, 3,3-dimethylpentyl, 2,2-dimethyl-3-methylbutyl, octyl, 2-methylheptyl, 3-methylheptyl, 4-methylheptyl, 2,2-dimethylhexyl, 2,3-dimethylhexyl, 2,4-dimethylhexyl, 3,3-dimethylhexyl, 2,2-dimethyl-3-methylpentyl, 2-methyl-3,3-dimethylpentyl, 2,3,4-trimethylpentyl and 2,2,3,3-tetramethylbutyl, 1-nonyl, 1-decyl, 1-undecyl or 1-dodecyl;

$C_1$-$C_{20}$-alkyl: e.g. $C_1$-$C_{12}$-alkyl as specified above, and also 1-tridecyl, 1-tetradecyl, 1-pentadecyl, 1-hexadecyl, 1-heptadecyl, 1-octadecyl, nonadecyl or eicosyl;

$C_3$- to $C_8$-cycloalkyl: e.g. cyclopropyl, cyclobutyl, cyclopentyl, cyclohexyl or cyclooctyl;

$C_3$- to $C_{12}$-cycloalkyl: $C_3$- to $C_8$-cycloalkyl as specified above, and also cyclododecyl;

$C_2$-$C_6$-alkenyl: e.g., ethenyl, propenyl, butenyl, pentenyl or hexenyl;

$C_2$-$C_{20}$-alkenyl: e.g. $C_2$-$C_6$-alkenyl as specified above, and also heptenyl, octenyl, nonenyl or decenyl;

$C_3$-$C_8$-cycloalkenyl: e.g. cyclopropenyl, cyclobutenyl, cyclopentenyl, or cyclohexenyl; aryl: mono- to tricyclic aromatic carbocycle having from 6 to 14 ring members, for example phenyl, naphthyl or anthracenyl;

heteroaryl: e.g. thienyl, furyl, pyrazolyl, imidazolyl, thiazolyl and oxazolyl; or $C_7$-$C_{12}$-aralkyl, for example phenylmethyl, 1-phenylethyl, 2-phenylethyl, 1-phenylpropyl, 2-phenylpropyl or 3-phenylpropyl.

The $R^1$ and $R^2$ radicals may optionally be substituted, the substituents being variable within a wide range.

$R^1$ and $R^2$ are preferably identically or each independently a straight-chain or branched hydrocarbon radical having from 1 or 3 to 20 carbon atoms, the hydrocarbon radical being saturated.

When secondary amines of the formula (I) whose substituents $R^1$ and/or $R^2$ comprise unsaturated bonds are used, hydrogenation of these substituents may also occur. Preference is given to using dimethylamine, diethylamine, di-n-propylamine, diisopropylamine, isopropylethylamine, di-n-butylamine, di-s-butylamine or dicyclohexylamine as secondary amines in the process.

Particular preference is given to using dimethylamine or diethylamine, especially preferably dimethylamine, in the reaction.

According to the invention, the molar ratio of acrolein to secondary amine is 2:1 or more. In general, the molar ratio of secondary amine to acrolein is in the range from 2:1 to 50:1, preferably from 2:1 to 10:1, more preferably from 2:1 to 5:1.

The reaction of acrolein with secondary amine can be effected without catalyst or in the presence of a catalyst.

Useful catalysts include, for example, solid Brønsted or Lewis acids, as described, for example, in EP-A1-449089 (page 2 column 2 lines 11-20) and in the article by Tanabe et al. (K. Tanabe, Studies in Surface Science and Catalysis, Vol. 51, 1989, p. 1 ff).

Examples here include acidic metal oxide catalysts, such as aluminum oxide, titanium dioxide, zirconium dioxide and silicon dioxide. Inorganic or organic ion exchangers laden with ammonium ions are also useful, such as zeolites or sulfonated copolymers of styrene and divinylbenzene (e.g. of the Lewatit® brand from Lanxess, Amberlite® brand from Rohm & Haas) or ion exchangers based on siloxane (for example of the Deloxan® brand from Degussa).

Acrolein can be reacted with secondary amine in the presence of a solvent, for example in ethers such as methyl tert-butyl ether, ethyl tert-butyl ether or tetrahydrofuran (THF); alcohols such as methanol, ethanol or isopropanol; hydrocarbons such as hexane, heptane or raffinate cuts; aromatics such as toluene; amides such as dimethylformamide or dimethylacetamide, or lactams such as N-methylpyrrolidone, N-ethylpyrrolidone, N-methylcaprolactam or N-ethylcaprolactam. Useful solvents also include suitable mixtures of the solvents listed above. THF is a preferred solvent. The solvent can be used in a proportion of from 5 to 95% by weight, preferably from 20 to 70%, more preferably from 30 to 60%, based in each case on the total weight of the reaction mixture, the total weight of the reaction mixture being composed of the sum of the masses of the starting materials and solvents used in the process.

Preference is given to performing the reaction of acrolein with secondary amine without an addition of solvent.

Acrolein is reacted with secondary amine at temperatures of from (−50) to 100° C., preferably from (−20) to 70° C., more preferably from (−10) to 40° C., and pressures of from 0.01 to 300 bar, preferably from 0.1 to 200 bar, more preferably from 1 to 200 bar, most preferably standard pressure (atmospheric pressure). In the case of gaseous secondary amines, such as dimethylamine, the reaction is performed preferably at pressures of from 5 to 400 bar, more preferably from 10 to 300 bar, especially from 15 to 200 bar.

The reaction of acrolein with secondary amine can be carried out either batchwise or continuously.

The batchwise reaction of acrolein with secondary amine can be effected, for example, in a stirred autoclave, a bubble column or a circulation reactor, for instance a jet loop reactor.

In the batchwise reaction of acrolein with secondary amine, typically secondary amine or a suspension of secondary amine and catalyst and if appropriate solvent is initially charged in the reactor. In order to ensure a high conversion and high selectivity, the suspension of secondary amine and catalyst is typically mixed thoroughly with acrolein, for example by means of a turbine stirrer in an autoclave.

The suspended catalyst material can be introduced and removed again with the aid of customary techniques (sedimentation, centrifugation, cake filtration, crossflow filtration). The catalyst can be used once or more than once.

When the reaction of acrolein with secondary amine is effected in the presence of a catalyst, the catalyst concentration is advantageously from 0.1 to 50% by weight, preferably from 0.5 to 40% by weight, more preferably from 1 to 30% by weight, especially from 5 to 20% by weight, based in each case on the total weight of the suspension consisting of secondary amine and catalyst.

The mean catalyst particle size is advantageously in the range from 0.001 to 1 mm, preferably in the range from 0.005 to 0.5 mm, especially from 0.01 to 0.25 mm.

The reaction of acrolein with secondary amine is preferably performed continuously, typically in pressure vessels or pressure vessel cascades.

Preference is given to passing acrolein and secondary amine through a tubular reactor, in which the catalyst is arranged in the form of a fixed bed.

In general, acrolein and the secondary amine are mixed thoroughly before being introduced into the pressure vessel or within the pressure vessel. The mixing can be effected, for example, before the introduction using static mixers.

In the pressure vessel, internals or mixing elements may also be introduced, which improve the mixing of acrolein and secondary amine. Mixing can, if appropriate, also be effected by means of installed stirrers or by pumped circulation of the reaction mixture. In the continuous reaction of acrolein with secondary amine, preference is given to establishing a catalyst hourly space velocity of from 0.01 to 10 kg, preferably from 0.05 to 7 kg and more preferably from 0.1 to 5 kg of acrolein per kg of catalyst and hour.

The reaction mixture obtained in stage a) comprises N,N,N',N'-substituted 1,3-propenediamine.

The reaction mixture obtained in stage a) can be worked up before use in stage b), in order to concentrate the N,N,N',N'-substituted 1,3-propenediamine, for example by distillation or rectification.

However, the reaction mixture obtained in stage a) is preferably, before use in stage b), used without additional purification or workup.

In stage b), the reaction mixture obtained in stage a) is reacted with hydrogen and ammonia in the presence of a hydrogenation catalyst.

Hydrogen is used in the process according to the invention.

The hydrogen is used generally in technically pure form. The hydrogen can also be used in the form of a hydrogen-comprising gas, i.e. in admixtures with other inert gases, such as nitrogen, helium, neon, argon or carbon dioxide. The hydrogen-comprising gases used may, for example, be reformer offgases, refinery gases, etc., when and provided that these gases do not comprise any catalyst poisons for the hydrogenation catalysts used, for example CO. However, preference is given to using pure hydrogen or essentially pure hydrogen in the process, for example hydrogen having a content of more than 99% by weight of hydrogen, preferably more than 99.9% by weight of hydrogen, more preferably more than 99.99% by weight of hydrogen, especially more than 99.999% by weight of hydrogen.

Ammonia is also used in the process according to the invention.

The ammonia used may be conventionally commercially available ammonia, for example ammonia having a content of more than 98% by weight of ammonia, preferably more than 99% by weight of ammonia, preferably more than 99.5% by weight, especially more than 99.9% by weight of ammonia.

The molar ratio of the ammonia used in stage b) to the acrolein used in stage a) is preferably from 1:1 to 1000:1, preferably from 2:1 to 100:1, more preferably from 4:1 to 50:1.

In a particular embodiment, stage b) is performed in the presence of water.

The amount of water is preferably selected such that the molar ratio of water to acrolein which was used in stage a) is in the range from 0.01:1 to 100:1, preferably in the range from 0.1:1 to 50:1, more preferably in the range from 0.5:1 to 10:1 and most preferably in the range from 1:1 to 5:1.

The water and the reaction mixture obtained in stage a) can be added together to stage b), for example as a premixed reactant stream, or separately. In the case of separate addition, water and the reaction mixture obtained in stage a) can be added to stage b) simultaneously, at different times or in succession. It is also possible that the addition of water is carried out actually before the performance of stage a) and is already present in stage a), since the presence of water does not adversely affect stage a). However, the water is preferably not added until before commencement of stage b).

The process according to the invention is performed in the presence of a hydrogenation catalyst which comprises cobalt.

The hydrogenation catalyst can be used in metallic form in the process.

Cobalt (Co) can be used in metallic form, for example in the form of a metal mesh or metal grid, as the hydrogenation catalyst.

In a preferred embodiment, Co in metallic form is used in the form of Raney sponge or skeletal catalysts as the hydrogenation catalyst in the process according to the invention.

Raney cobalt hydrogenation catalysts are prepared typically by treating an aluminum-cobalt alloy with concentrated sodium hydroxide solution, which leaches out the aluminum and gives rise to a metallic cobalt sponge. The preparation of Raney hydrogenation catalysts is described, for example, in the Handbook of Heterogeneous Catalysis (M. S. Wainright in G. Ertl, H. Knözinger, J. Weitkamp (eds.), Handbook of Heterogeneous Catalysis, Vol. 1, Wiley-VCH, Weinheim, Germany 1997, page 64 ff.). Such catalysts are obtainable, for example, as Raney® catalysts from Grace or as Sponge Metal® catalysts from Johnson Matthey.

The molar proportion of cobalt atoms based on the sum of all metal atoms in the hydrogenation catalyst used, which has been used in the process in metallic form, is preferably 50 mol % or more, more preferably 75 mol %, even more preferably 90 mol % or more, especially preferably 99 mol % or more. The composition of the hydrogenation catalyst which is used in metallic form can be measured by means of atomic absorption spectrometry (AAS), atomic emission spectrometry (AES), X-ray fluorescence analysis (RFA) or ICP-OES (Inductively Coupled Plasma Optical Emission Spectrometry).

The hydrogenation catalysts useable in the process according to the invention can also be prepared by reducing so-called catalyst precursors.

The catalyst precursor comprises an active material which comprises one or more catalytically active components and optionally a carrier material.

The catalytically active components are oxygen compounds of the metals of groups 8 and/or 9 and/or 10 and/or 11 of the Periodic Table of the Elements (Periodic Table in the IUPAC version of Jun. 22, 2007), for example their metal oxides or hydroxides (if appropriate examples), such as CoO, NiO, $Mn_3O_4$, CuO, $RuO(OH)_x$ and/or mixed oxides thereof.

According to the invention, the catalyst precursor of the hydrogenation catalyst comprises oxygen compounds of cobalt as the catalytically active component, for example in the form of CoO and/or in the form of a mixed oxide of cobalt, such as $LiCoO_2$. The catalyst precursor of the hydrogenation catalyst preferably comprises CoO as the catalytically active component.

As well as oxygen compounds of cobalt, the catalyst precursor of the hydrogenation catalyst may comprise further catalytically active components.

The compositions specified below are based on the composition of the catalyst precursor after the last heat treatment thereof, which is generally a calcination and/or another heat treatment, and before the reduction thereof with hydrogen.

The mass of the active material is the sum of the mass of the support material and of the mass of the catalytically active components, i.e. the support material is considered to form part of the active material.

The molar proportion of cobalt atoms based on the sum of all metal atoms which are present in the catalytically active components used is preferably 10 mol % or more, more preferably 30 mol % or more, even more preferably 50 mol % or more, especially 90 mol % or more.

The atomic composition of the catalytically active components can be measured by means of atomic absorption spectrometry (AAS), atomic emission spectrometry (AES), X-ray fluorescence analysis (RFA) or ICP-OES (Inductively Coupled Plasma Optical Emission Spectrometry).

The proportion of the active material based on the total mass of the catalyst precursor is typically 70% by weight or more, preferably from 80 to 100% by weight, more preferably from 90 to 99% by weight, especially from 92 to 98% by weight.

The catalyst precursor may, as well as the active material, comprise further components, such as shaping agents, for example graphite, stearic acid, phosphoric acid or further processing assistants.

The catalyst precursor may further comprise, as further components, as well as the active material, one or more doping elements (oxidation state 0) or inorganic or organic compounds thereof, selected from groups 1 to 14 of the Periodic Table. Examples of such elements or compounds thereof are:

transition metals, such as Mn or manganese oxides, Re or rhenium oxides, Cr or chromium oxides, Mo or molybdenum oxides, W or tungsten oxides, Ta or tantalum oxides, Nb or niobium oxides or niobium oxalate, V or vanadium oxides or vanadylpyrophosphate, zinc or zinc oxides, lanthanides such as Ce or $CeO_2$ or Pr or $Pr_2O_3$, alkali metal oxides such as $K_2O$, alkali metal carbonates such as $Na_2CO_3$ and $K_2CO_3$, alkaline earth metal oxides such as SrO, alkaline earth metal carbonates such as $MgCO_3$, $CaCO_3$, $BaCO_3$, phosphoric anhydrides and boron oxide ($B_2O_3$).

In a preferred embodiment, the active material of the catalyst precursor does not comprise any support material.

Such catalyst precursors are, for example, catalysts which are disclosed in patent application PCT/EP2007/052013 and comprise, before the reduction with hydrogen, a) cobalt and b) one or more elements of the alkali metal group, of the alkaline earth metal group, of the group of the rare earths or zinc or mixtures thereof, where the elements a) and b) are present at least partly in the form of their mixed oxides, for example $LiCoO_2$, or catalysts which are disclosed in EP-A-0636409 and whose catalytically active material, before the reduction with hydrogen, comprises from 55 to 98% by weight of Co, calculated as CoO, from 0.2 to 15% by weight of phosphorus, calculated as $H_3PO_4$, from 0.2 to 15% by weight of manganese, calculated as $MnO_2$, and from 0.2 to 15% by weight of alkali metal, calculated as $M_2O$ (M=alkali metal), or catalysts which are disclosed in EP-A-0742045 and whose catalytically active material, before the reduction with hydrogen, comprises from 55 to 98% by weight of Co, calculated as CoO, from 0.2 to 15% by weight of phosphorus, calculated as $H_3PO_4$, from 0.2 to 15% by weight of manganese, calculated as MnO2, and from 0.05 to 5% by weight of alkali metal, calculated as $M_2O$ (M=alkali metal).

Catalyst precursors which comprise mixed oxides of cobalt, such as $LiCoO_2$, and which preferably do not comprise any support material, can generally be prepared by thermal treatment of the corresponding compounds of cobalt and one or more compounds of the alkali metal group, of compounds of the alkaline earth metal group, of compounds from the group of the rare earths or of compounds of zinc, for example the nitrates, carbonates, hydroxides, oxides, acetates, oxalates or citrates. Thermal treatment can be understood, for example, as the co-melting or calcination of the above-mentioned compounds. The thermal treatment of the abovementioned compounds, such as the nitrates, carbonates, hydroxides, oxides, can be effected under air. In a preferred embodiment, the thermal treatment, especially of the carbonates, is effected under an inert gas atmosphere. Examples of suitable inert gases include nitrogen, carbon dioxide, helium, neon, argon, xenon, krypton or mixtures of the inert gases mentioned. Nitrogen is preferentially suitable.

Processes for preparing $LiCoO_2$ are described, for example, in Antolini [E. Antolini, Solid State Ionics, 159-171 (2004)] and Fenton et al. [W. M. Fenton, P. A. Huppert, Sheet Metal Industries, 25 (1948), 2255-2259).

The catalyst precursor used, which preferably does not comprise any support material, may also be $LiCoO_2$, which is obtained by recycling batteries. A method of recycling or recovering lithium cobaltite from used batteries can be derived, for example, from CN-A-1594109. Mechanical opening of the battery and the leaching out of aluminum constituents with conc. NaOH can provide an $LiCoO_2$-rich filtercake.

In a further preferred embodiment, the active material comprises—in addition to the catalytically active components—support material.

The support materials used are preferably carbon, such as graphite, carbon black and/or activated carbon, aluminum oxide (gamma, delta, theta, alpha, kappa, chi or mixtures thereof), silicon dioxide, zirconium dioxide, zeolites, aluminosilicates, etc., and mixtures of these support materials.

The proportion of support material in the active material can vary over a wide range according to the preparation method selected.

In the case of catalyst precursors which are prepared by impregnation, the proportion of support material in the active material is generally more than 50% by weight, preferably more than 75% by weight and more preferably more than 85% by weight. In the case of catalyst precursors which are prepared by precipitation reactions, such as coprecipitation or application by precipitation, the proportion of support material in the active material is generally in the range from 10 to 90% by weight, preferably in the range from 15 to 80% by weight and more preferably in the range from 20 to 70% by weight.

Preferred catalyst precursors which are obtained by precipitation reactions are, for example, the catalysts which are disclosed in EP-A-963 975 and whose catalytically active material, before the reduction with hydrogen, comprises from 22 to 40% by weight of $ZrO_2$, from 1 to 30% by weight of oxygen compounds of copper, calculated as CuO, from 15 to 50% by weight of oxygen compounds of nickel, calculated as NiO, where the molar Ni:Cu ratio is greater than 1, from 15 to 50% by weight of oxygen compounds of cobalt, calculated as CoO, from 0 to 10% by weight of oxygen compounds of aluminum and/or of manganese, calculated as $Al_2O_3$ and $MnO_2$ respectively, and no oxygen compounds of molybdenum, for example the catalyst A which is disclosed in loc. cit., page 17, and has the composition of 33% by weight of Zr, calculated as $ZrO_2$, 28% by weight of Ni, calculated as NiO, 11% by weight of Cu, calculated as CuO, and 28% by weight of Co, calculated as CoO;

catalysts which are disclosed in EP-A2-1106600 and whose catalytically active material, before the reduction with hydrogen, comprises from 22 to 45% by weight of oxygen compounds of zirconium, calculated as $ZrO_2$, from 1 to 30% by weight of oxygen compounds of copper, calculated as CuO, from 5 to 50% by weight of oxygen compounds of nickel, calculated as NiO, where the molar ratio of nickel to copper is greater than 1, from 5 to 50% by weight of oxygen compounds of cobalt, calculated as CoO, from 0 to 5% by weight of oxygen compounds of molybdenum, calculated as $MoO_3$, and from 0 to 10% by weight of oxygen compounds of aluminum and/or of manganese, calculated as $Al_2O_3$ and $MnO_2$ respectively;

catalysts which are disclosed in WO-A-03/076386 and whose catalytically active material, before the reduction with hydrogen, comprises from 22 to 40% by weight of oxygen compounds of zirconium, calculated as $ZrO_2$, from 1 to 30% by weight of oxygen compounds of copper, calculated as CuO, from 15 to 50% by weight of oxygen compounds of nickel, calculated as NiO, where the molar ratio of nickel to copper is greater than 1, from 15 to 50% by weight of oxygen compounds of cobalt, calculated as CoO, and less than 1% by weight of alkali metal, calculated as alkali metal oxide;

catalysts which are disclosed in EP-A-1852182 and comprise cobalt on a ZnO support and have the following particle size distribution: <10% of the particles have a particle size below one μm, 70-99% of the particles have a particle size between 1 and 5 μm and <20% of the particles have a particle size of more than 5 μm.

The catalyst precursors which do not comprise any support material, and also the catalyst precursors which comprise support material can be prepared by known processes, for example by precipitation, application by precipitation or impregnation.

In a preferred embodiment, catalyst precursors which are prepared by impregnation of support materials (impregnated catalyst precursors) are used in the process according to the invention.

The support materials which are used in the impregnation can be used, for example, in the form of powders or shaped bodies, such as extrudates, tablets, spheres or rings. Support material suitable for fluidized bed reactors is preferably obtained by spray drying.

Useful support materials include, for example, carbon, such as graphite, carbon black and/or activated carbon, aluminum oxide (gamma, delta, theta, alpha, kappa, chi or mixtures thereof), silicon dioxide, zirconium dioxide, zeolites, aluminosilicates or mixtures thereof.

The abovementioned support materials can be impregnated by the customary processes (A. B. Stiles, Catalyst Manufacture—Laboratory and Commercial Preparations, Marcel Dekker, New York, 1983), for example by applying a metal salt solution in one or more impregnation stages. Useful metal salts generally include water-soluble metal salts, such as the nitrates, acetates or chlorides of the catalytically active components or doping elements in question, such as cobalt nitrate or cobalt chloride. Thereafter, the impregnated support material is generally dried and if appropriate calcined.

The impregnation can also be effected by the so-called "incipient wetness method", in which the support material, according to its water absorption capacity, is moistened with the impregnation solution up to saturation at most. However, the saturation can also be effected in supernatant solution.

In the case of multistage impregnation processes, it is appropriate to dry and if appropriate to calcine between individual impregnation steps. Multistage impregnation should advantageously be employed when the support material is to be contacted with metal salts in a relatively large amount.

To apply a plurality of metal components to the support material, the impregnation can be effected simultaneously with all metal salts or in any sequence of the individual metal salts in succession.

In a further preferred embodiment, catalyst precursors are prepared by means of a coprecipitation of all of their components. To this end, a soluble compound of the appropriate active component, the doping elements and if appropriate a soluble compound of a support material in a liquid are admixed with a precipitant under hot conditions and with stirring until precipitation is complete.

The liquid used is generally water.

Useful soluble compounds of the active components include typically the corresponding metal salts, such as the nitrates, sulfates, acetates or chlorides, of the metals of groups 8 and/or 9 and/or 10 and/or 11 of the Periodic Table of the Elements (Periodic Table in the IUPAC version of Jun. 22, 2007), especially of Co.

The water-soluble compounds of a support material used are generally water-soluble compounds of Ti, Al, Zr, Si, etc., for example the water-soluble nitrates, sulfates, acetates or chlorides of these elements.

The water-soluble compounds of the doping elements used are generally water-soluble compounds of the doping elements, for example the water-soluble nitrates, sulfates, acetates or chlorides of these elements.

Catalyst precursors can also be prepared by application by precipitation.

Application by precipitation is understood to mean a preparation method in which a sparingly soluble or insoluble support material is suspended in a liquid and then soluble compounds, such as soluble metal salts, of the corresponding metal oxides are added, which are then precipitated onto the suspended support by adding a precipitant (for example described in EP-A2-1 106 600, page 4, and A. B. Stiles, Catalyst Manufacture, Marcel Dekker, Inc., 1983, page 15).

Examples of sparingly soluble and insoluble support materials include carbon compounds, such as graphite, carbon black and/or activated carbon, aluminum oxide (gamma, delta, theta, alpha, kappa, chi or mixtures thereof), silicon dioxide, zirconium dioxide, zeolites, aluminosilicates or mixtures thereof.

The support material is generally present in the form of powder or spall.

The liquid used, in which the support material is suspended, is typically water.

Useful soluble compounds include the aforementioned soluble compounds of the active components or of the doping elements.

In the precipitation reactions, the type of soluble metal salts used is generally not critical. Since the principal factor in this procedure is the water solubility of the salts, one criterion is their good water solubility, which is essential for the preparation of these comparatively highly concentrated salt solutions. It is considered to be obvious that, in the selection of the salts of the individual components, of course only salts with those anions which do not lead to disruption, whether by causing undesired precipitation reactions or by complicating or preventing precipitation by complexation, are selected.

Typically, in the precipitation reactions, the soluble compounds are precipitated as sparingly soluble or insoluble, basic salts by adding a precipitant.

The precipitants used are preferably aqueous alkalis, especially mineral bases, such as alkali metal bases. Examples of precipitants are sodium carbonate, sodium hydroxide, potassium carbonate or potassium hydroxide.

The precipitants used may also be ammonium salts, for example ammonium halides, ammonium carbonate, ammonium hydroxide or ammonium carboxylates.

The precipitation reactions can be carried out, for example, at temperatures of from 20 to 100° C., particularly from 30 to 90° C., especially from 50 to 70° C.

The precipitates obtained in the precipitation reactions are generally chemically inhomogeneous and comprise generally mixtures of the oxides, oxide hydrates, hydroxides, carbonates and/or hydrogencarbonates of the metals used. It may be found to be favorable for the filterability of the precipitates when they are aged, i.e. when they are left for a certain time after the precipitation, if appropriate under hot conditions or while passing air through.

The precipitates obtained by these precipitation processes are typically processed by washing, drying, calcining and conditioning them.

After washing, the precipitates are dried generally at from 80 to 200° C., preferably from 100 to 150° C., and then calcined.

The calcination is performed generally at temperatures between 300 and 800° C., preferably from 400 to 600° C., especially at from 450 to 550° C.

After the calcination, the catalyst precursors obtained by precipitation reactions are typically conditioned.

The conditioning can be effected, for example, by adjusting the precipitated catalyst to a particular particle size by grinding.

After the grinding, the catalyst precursor obtained by precipitation reactions can be mixed with shaping assistants, such as graphite or stearic acid, and processed further to shaped bodies.

Common processes for shaping are described, for example, in the Ullmann [Ullmann's Encyclopedia Electronic Release 2000, chapter: "Catalysis and Catalysts", pages 28-32] and by Ertl et al. [Ertl, Knözinger, Weitkamp, Handbook of Heterogeneous Catalysis, VCH Weinheim, 1997, pages 98 ff.].

As described in the references cited, the process for shaping can be used to obtain shaped bodies in any three-dimensional shape, for example round, angular, elongated or the like, for example in the form of extrudates, tablets, granule, spheres, cylinders or pellets. Common processes for shaping are, for example, extrusion, tableting, i.e. mechanical pressing or pelletization, i.e. compaction by circular and/or rotating motions.

The conditioning or shaping is generally followed by a heat treatment. The temperatures in the heat treatment correspond typically to the temperatures in the calcination.

The catalyst precursors obtained by precipitation reactions comprise the catalytically active components in the form of a mixture of their oxygen compounds, i.e. especially as oxides, mixed oxides and/or hydroxides. The catalyst precursors thus prepared can be stored as such.

Before their use as hydrogenation catalysts in stage b), catalyst precursors which have been obtained as described above by impregnation or precipitation are generally prereduced by treatment with hydrogen after the calcination or conditioning.

For the prereduction, the catalyst precursors are generally first exposed to a nitrogen-hydrogen atmosphere at from 150 to 200° C. over a period of from 12 to 20 hours and then treated in a hydrogen atmosphere at from 200 to 400° C. for another up to approx. 24 hours. This prereduction reduces some of the oxygen-containing metal compounds present in the catalyst precursors to the corresponding metals, such that they are present together with the different kinds of oxygen compounds in the active form of the hydrogenation catalyst.

In a preferred embodiment, the prereduction of the catalyst precursor is undertaken in the same reactor in which stage b) is subsequently performed.

The hydrogenation catalyst thus formed can, after the prereduction, be handled and stored under an inert gas such as nitrogen, or under an inert liquid, for example an alcohol, water or the product of the particular reaction for which the hydrogenation catalyst is used. After the prereduction, the hydrogenation catalyst can also be passivated, i.e. provided with a protective oxide layer, with an oxygen-comprising gas stream such as air or a mixture of air with nitrogen.

The storage of the hydrogenation catalysts which have been obtained by prereduction of catalyst precursors under inert substances, or the passivation of the hydrogenation catalyst, enable uncomplicated and safe handling and storage of the catalyst. If appropriate, the hydrogenation catalyst then has to be freed of the inert liquid before the start of the actual reaction, or the passivation layer has to be removed, for example by treating with hydrogen or a hydrogen-comprising gas.

Before it is used in stage b), the hydrogenation catalyst can be freed from the inert liquid or passivation layer. This is done, for example, by the treatment of the hydrogenation catalyst with hydrogen or a hydrogen-comprising gas. Preference is given to undertaking stage b) directly after the treatment of the hydrogenation catalyst in the same reactor in which the hydrogenation catalyst was also treated with hydrogen or a hydrogen-comprising gas.

Catalyst precursors can, however, also be used in the process without prereduction, in which case they are reduced by the hydrogen present in the reactor under the conditions of the hydrogenation which takes place in stage b), which generally forms the hydrogenation catalyst in situ.

The performance of stage b) (hydrogenation stage) can be performed batchwise or preferably continuously.

The performance of stage b) can be performed in the liquid phase or in the gas phase. Preference is given to performing stage b) in the liquid phase.

The reaction mixture obtained in stage a) can be reacted with hydrogen and ammonia in the presence of a solvent, preference being given to using the solvent which has already been used beforehand in stage a), for example in ethers such as methyl tert-butyl ether, ethyl tert-butyl ether or tetrahydrofuran (THF); alcohols such as methanol, ethanol or isopropanol; hydrocarbons such as hexane, heptane or raffinate cuts; aromatics such as toluene; amides such as dimethylformamide or dimethylacetamide, or lactams such as N-methylpyrrolidone, N-ethylpyrrolidone, N-methylcaprolactam or N-ethylcaprolactam. Useful solvents also include suitable mixtures of the solvents listed above. The solvent can be used in a proportion of from 5 to 95% by weight, preferably from 20 to 70%, more preferably from 30 to 60%, based in each case on the total weight of the reaction mixture from stage a) and solvent.

Preference is given to performing the reaction of acrolein with secondary amine without an addition of solvent.

The batchwise performance of the hydrogenation stage (stage b)) can be performed, for example, in a stirred autoclave, a bubble column or a circulation reactor, for instance a jet loop reactor.

In the batchwise performance of the hydrogenation stage, a suspension of the reaction mixture from stage a) and catalyst and if appropriate solvent is typically initially charged in the reactor. In order to ensure a high conversion and high selectivity, the suspension of the reaction mixture from stage a) and catalyst with ammonia is typically mixed thoroughly, for example by means of a turbine stirrer in an autoclave. The suspended catalyst material can be introduced and removed again with the aid of customary techniques (sedimentation, centrifugation, cake filtration, crossflow filtration). The catalyst can be used once or more than once.

The catalyst concentration is advantageously from 0.1 to 50% by weight, preferably from 0.5 to 40% by weight, more preferably from 1 to 30% by weight, especially from 5 to 20% by weight, based in each case on the total weight of the suspension consisting of the reaction mixture from stage a) and catalyst.

The mean catalyst particle size is advantageously in the range from 0.001 to 1 mm, preferably in the range from 0.005 to 0.5 mm, especially from 0.01 to 0.25 mm. In the case of batchwise performance of stage b), the pressure is generally 1-400 bar, preferably from 10 to 300 bar, more preferably from 20 to 250 bar. The temperature is generally from 40 to 400° C., preferably from 50 to 200° C., more preferably from 60 to 150° C., especially from 60 to 120° C.

The hydrogenation stage is preferably performed continuously, typically in pressure vessels or pressure vessel cascades.

In the case of continuous performance of stage b) in the liquid phase, the reaction mixture from stage a) including hydrogen and ammonia is preferably passed over the catalyst, which is preferably present in a fixed bed reactor. Both trickle mode and liquid phase mode are possible.

In the case of continuous performance of stage b) in the liquid phase, the pressure is generally 1-400 bar, preferably from 10 to 300 bar, more preferably from 20 to 250 bar. The temperature is generally from 40 to 400° C., preferably from 50 to 200° C., more preferably from 60 to 150° C., especially from 60 to 120° C.

In the case of continuous performance of stage b) in the gas phase, the reaction mixture from stage a) is passed over the catalyst together with ammonia in a gas stream selected on a sufficiently large scale for evaporation, in the presence of hydrogen.

In the case of performance of stage b) in the gas phase, the pressure is generally 0.1-400 bar, preferably from 1 to 100 bar, more preferably from 1 to 50 bar. The temperature is generally from 40 to 400° C., preferably from 50 to 200° C., more preferably from 60 to 150° C., especially from 60 to 120° C.

The catalyst hourly space velocity in the case of continuous performance of stage b) is generally in the range from 0.05 to 20 kg, preferably from 0.1 to 15 kg and more preferably from 0.2 to 10 kg of reaction mixture from stage a) per liter of catalyst (bed volume) and hour.

The reaction mixture obtained in stage b) comprises N,N-substituted 1,3-propenediamine.

Before further use or further processing, the reaction mixture obtained in stage b) can be worked up in order to concentrate the N,N-substituted 1,3-propanediamine, for example by distillation or rectification.

Unconverted reactants, such as secondary amines, hydrogen or ammonia, can be recycled into the process.

DMAPA prepared in accordance with the invention constitutes an important intermediate for the industrial production, for example, of lubricant soaps and other detergents. DMAPA additionally serves as a starting material for the production of coagulants and is itself said to have anticorrosive properties. It also serves to prepare comb polymers which are used as an additive in the construction industry, and other polymers with antimicrobial properties. The present invention accordingly also relates to the use of the DMAPA obtainable in accordance with the invention in the aforementioned fields of use.

One advantage of the invention lies in the provision of a process for preparing N,N-substituted 1,3-propanediamines from acrolein, wherein a higher selectivity based on the acrolein used is achieved as compared with the prior art. In addition, the formation of by-products, such as 3-methylpiperidine and N,N,N',N'-substituted 1,3-propanediamines, which are obtained in the hydrogenation of the N,N,N',N'-substituted 1,3-propenediamines formed as an intermediate, can be reduced. By virtue of the fact that the N,N,N',N'-substituted 1,3-propenediamines obtained as an intermediate need not be isolated or purified before the further conversion to N,N-substituted 1,3-propanediamine, the process is easy to handle and industrially implementable. The present invention provides a new preparation route for DMAPA, in which feedstocks which can be obtained on the basis of renewable raw materials are used.

The invention is illustrated in detail by the examples which follow.

EXAMPLE 1

A 270 ml autoclave was initially charged with 67.6 g of dimethylamine (1.5 mol), and 16.8 g of acrolein (0.3 mol) were pumped in while cooling (4° C.) over 60 minutes. The mixture was stirred for 15 minutes. A sample was taken and analyzed by means of gas chromatography. Then the contents of this autoclave were transferred by means of a connecting line, by injection of hydrogen, into a 270 ml high-pressure autoclave which had been heated to 100° C. beforehand and which had already been initially charged with 1.8 g of Ra—Co (THF-washed) in 51.0 g of $NH_3$ (3.0 mol) and 10.8 g of water (0.6 mol). The temperature of the second autoclave was held at 100° C. and hydrogen was injected to 60 bar. Then hydrogenation was effected for 2 hours and the pressure was maintained by adding hydrogen. After 2 hours, a sample was taken and analyzed by means of gas chromatography. The chromatogram showed full conversion of acrolein and of the enamine which occurred as the intermediate, and a DMAPA yield of 91.4%. The dimethylaminopropanol (DMAPOL) yield (measured in GC area %) was 0.4%. The yields of the compounds were determined by means of gas chromatography as area percentages (a %).

EXAMPLE 2

A 270 ml autoclave was initially charged with 67.6 g of dimethylamine (1.5 mol), and 16.8 g of acrolein (0.3 mol) were pumped in while cooling (4° C.) over 60 minutes. The mixture was stirred for 15 minutes. A sample was taken and analyzed by means of gas chromatography. Then the contents of this autoclave were transferred by means of a connecting line, by injection of hydrogen, into a 270 ml high-pressure autoclave which had already been initially charged with 1.8 g of Ra—Co (THF-washed) in 51.0 g of $NH_3$ (3.0 mol) and 10.8 g of water (0.6 mol). The second autoclave was heated to 80° C., and hydrogen was injected to 60 bar. Then hydrogenation was effected for 2 hours and the pressure was maintained by adding hydrogen. After 2 hours, a sample was taken and analyzed by means of gas chromatography. The chromatogram showed full conversion of acrolein and of the enamine which occurred as the intermediate, and a DMAPA yield of 80.3%. The dimethylaminopropanol (DMAPOL) yield was 13.9%. The yields of the compounds were determined by means of gas chromatography as area percentages (a %).

EXAMPLE 3

A 270 ml autoclave was initially charged with 33.8 g of dimethylamine (0.75 mol) in 30 g of THF, and 16.8 g of acrolein (0.3 mol) dissolved in 30 g of THF were pumped in while cooling (4° C.) over 60 minutes. The mixture was stirred for 15 minutes. A sample was taken and analyzed by means of gas chromatography. Then the contents of this autoclave were transferred by means of a connecting line, by injection of hydrogen, into a 270 ml high-pressure autoclave which had already been initially charged with 1.8 g of Ra—Co (THF-washed) in 25.5 g of $NH_3$ (1.5 mol). The second autoclave was heated to 80° C., and hydrogen was injected to 60 bar. Then hydrogenation was effected for 2 hours and the pressure was maintained by adding hydrogen. After 6 hours, a sample was taken and analyzed by means of gas chromatography. The chromatogram showed full conversion of acrolein and of the enamine which occurred as the intermediate, and a DMAPA yield of 88.7%. The dimethylaminopropanol (DMAPOL) yield was 0.8%. The yields of the compounds were determined by means of gas chromatography as area percentages (a %).

EXAMPLE 4

A 270 ml autoclave was initially charged with 67.6 g of dimethylamine (1.5 mol), and 16.8 g of acrolein (0.3 mol) were pumped in while cooling (4° C.) over 60 minutes. The mixture was stirred for 15 minutes. A sample was taken and analyzed by means of gas chromatography. Then the contents of this autoclave were transferred by means of a connecting line, by injection of hydrogen, into a 270 ml high-pressure autoclave which had been heated beforehand to 120° C. and which had already been initially charged with 1.8 g of Ra—Co (THF-washed) in 51.0 g of $NH_3$ (3.0 mol) and 10.8 g of water (0.6 mol). The temperature of the second autoclave was held at 120° C. and hydrogen was injected to 100 bar. Then hydrogenation was effected for 2 hours and the pressure was maintained by adding hydrogen. After 3 hours, a sample was taken and analyzed by means of gas chromatography. The chromatogram showed full conversion of acrolein and of the enamine which occurred as the intermediate, and a DMAPA yield of 87.8%. The dimethylaminopropanol (DMAPOL) yield was 0.8%. The yields of the compounds were determined by means of gas chromatography as area percentages (a %).

EXAMPLE 5

A 270 ml autoclave was initially charged with 67.6 g of dimethylamine (1.5 mol), and 16.8 g of acrolein (0.3 mol) were pumped in while cooling (4° C.) over 60 minutes. The mixture was stirred for 15 minutes. A sample was taken and analyzed by means of gas chromatography. Then the contents of this autoclave were transferred by means of a connecting line, by injection of hydrogen, into a 270 ml high-pressure autoclave which had already been initially charged with 1.8 g of Ra—Co (THF-washed) in 51.0 g of $NH_3$ (3.0 mol) and 10.8 g of water (0.6 mol). The second autoclave was heated to 60° C., and hydrogen was injected to 60 bar. Then hydrogenation was effected for 2 hours and the pressure was maintained by adding hydrogen. After 3 hours, a sample was taken and analyzed by means of gas chromatography. The chromatogram showed full conversion of acrolein and of the enamine which occurred as the intermediate, and a DMAPA yield of 58.2%. The dimethylaminopropanol (DMAPOL) yield was 33.8%. The yields of the compounds were determined by means of gas chromatography as area percentages (a %).

EXAMPLE 6

A 270 ml autoclave was initially charged with 67.6 g of dimethylamine (1.5 mol), and 16.8 g of acrolein (0.3 mol) were pumped in while cooling (4° C.) over 60 minutes. The mixture was stirred for 15 minutes. A sample was taken and analyzed by means of gas chromatography. Then the contents of this autoclave were transferred by means of a connecting line, by injection of hydrogen, into a 270 ml high-pressure autoclave which had already been initially charged with 1.8 g of Ra—Co (THF-washed) in 51.0 g of $NH_3$ (3.0 mol). The second autoclave was heated to 60° C., and hydrogen was injected to 60 bar. Then hydrogenation was effected for 2 hours and the pressure was maintained by adding hydrogen. After 3 hours, a sample was taken and analyzed by means of gas chromatography. The chromatogram showed full conversion of acrolein and of the enamine which occurred as the intermediate, and a DMAPA yield of 50.4%. The dimethylaminopropanol (DMAPOL) yield was 29.1%. The yields of the compounds were determined by means of gas chromatography as area percentages (a %).

EXAMPLE 7

A 100 ml flask was initially charged with 18.25 g of anhydrous diethylamine (0.25 mol) and 10 g of THF, and 5.6 g of acrolein (0.1 mol) in 10 g of THF were added dropwise while cooling (4° C.). The mixture was charged into a 160 ml high-pressure autoclave; 0.6 g of ™Ra—Co (THF-washed) was added, the autoclave was closed and then 8.5 g of ammonia (0.5 mol) were added. The autoclave was heated to 80° C. and, on attainment of the desired reaction temperature, $H_2$ was injected up to 60 bar. After 6 hours, it was found by gas chromatography analysis that 87% of the desired N,N-diethyl-1,3-propanediamine product had formed. No 3-methylpiperidine was found.

COMPARATIVE EXAMPLE 7a:

In the case of use of Raney nickel in the same amount instead of Raney cobalt and under otherwise identical experimental conditions to those in Example 7, a selectivity of 81.3% for N,N-diethyl-1,3-propanediamine is found.

COMPARATIVE EXAMPLE 7b:

The experimental conditions corresponded to the conditions of Example 7, with the difference that only 9.2 g of anhydrous diethylamine (0.125 mol) were used in the reaction in place of 18.25 g of anhydrous diethylamine (0.25 mol).

It was found by gas chromatography analysis of a sample that 52 GC area % of the desired N,N-diethyl-1,3-propanediamine product had formed. In addition, 8 GC area % of 3-methylpiperidine was found.

EXAMPLE 8

A 270 ml autoclave was initially charged with 33.8 g of dimethylamine (0.75 mol) and 30 g of THF, and 16.8 g of acrolein (0.3 mol) in 30 g of THF were pumped in while cooling (4° C.) over 60 minutes. The mixture was stirred for 15 minutes. A sample was taken and analyzed by means of gas chromatography. The contents of this autoclave were then transferred by means of a connecting line, by injecting hydrogen, to a 270 ml high-pressure autoclave which had already been initially charged with 1.8 g of Ra—Co (THF-washed) in 25.5 g of $NH_3$ (1.5 mol). The second autoclave was heated to 80° C. and hydrogen was injected to 60 bar. Hydrogenation was then effected for 3 hours and the pressure was maintained by adding hydrogen. After 3 hours, a sample was taken and analyzed by means of gas chromatography. The chromatogram showed full conversion of acrolein and of the enamine which occurred as an intermediate, and a selectivity for DMAPA of 88.3%.

COMPARATIVE EXAMPLE 8a:

In the case of use of Raney nickel in the same amount instead of Raney cobalt and under otherwise identical experimental conditions to those in Example 2, a selectivity of 57.5% for DMAPA is found.

The invention claimed is:

1. A process for preparing N,N-substituted 1,3-propanediamine which comprises
    a) reacting a secondary amine with an acrolein at a temperature of from −50 to 100° C. and a pressure of from 0.01 to 300 bar, and
    b) reacting the reaction mixture obtained in stage a) with hydrogen and ammonia in the presence of a hydrogenation catalyst at a temperature of from 40 to 400° C. and a pressure of from 1 to 400 bar,
    wherein the molar ratio of secondary amine to acrolein in stage a) is 2:1 or more and the hydrogenation catalyst used in stage b) comprises cobalt.

2. The process according to claim 1, wherein stage b) is performed in the presence of water.

3. The process according to claim 1, wherein the molar ratio of water to acrolein used is in the range from 0.5:1 to 10:1.

4. The process according to claim 1, wherein stage b) is performed at a temperature of from 50 to 200° C. and at a pressure of from 20 to 250 bar.

5. The process according to claim 1, wherein the molar ratio of the ammonia used in stage b) to the acrolein used in stage a) is from 2:1 to 100:1.

6. The process according to claim 1, wherein the hydrogenation catalyst is present in metallic form.

7. The process according to claim 6, wherein the molar proportion of cobalt atoms based on the sum of all metal atoms in the hydrogenation catalyst used, which has been used in the process in metallic form, is 50 mol % or more.

8. The process according to claim 6, wherein the hydrogenation catalyst in metallic form is a Raney sponge or skeletal catalyst.

9. The process according to claim 1, wherein the hydrogenation catalyst is obtained by reducing catalyst precursors which comprise one or more catalytically active components in the form of oxygen compounds of groups 8 and/or 9 and/or 10 and/or 11 of the Periodic Table of the Elements.

10. The process according to claim 9, wherein the molar proportion of cobalt atoms based on the sum of all metal atoms which are present in the catalytically active components used is 30 mol % or more.

11. The process according to claim 1, wherein the reaction mixture obtained in stage a), before use in stage b), is used without additional purification or workup.

12. The process according to claim 1, wherein said secondary amine is dimethylamine, diethylamine, dipropylamine, diisopropylamine, dibutylamine, diisobutylamine, dihexylamine or dicyclohexylamine.

13. The process according to claim 12, wherein the secondary amine is dimethylamine or diethylamine or a mixture thereof.

14. The process according to claim 1, wherein the acrolein is obtained by dehydrating glycerol and said glycerol is obtained by the conversion of fats and oils to fatty acids or fatty acid methyl esters.

15. A process for the preparation of lubricant soaps or other detergents, coagulants, polymers or comb polymers which comprises the following steps:
   a) producing the N,N-Dimethyl-1,3-propanediamine (DMAPA) according to claim 1, and
   b) reacting said DMAPA from step a) to form lubricant soaps or detergents, coagulants, polymers or comb polymers.

* * * * *